United States Patent
Pfefferbaum et al.

(10) Patent No.: US 6,819,952 B2
(45) Date of Patent: Nov. 16, 2004

(54) MAGNETIC RESONANCE SPECTROSCOPIC IMAGING METHOD TO MONITOR PROGRESSION AND TREATMENT OF NEURODEGENERATIVE CONDITIONS

(75) Inventors: Adolf Pfefferbaum, Los Altos Hills, CA (US); Elfar Adalsteinsson, Palo Alto, CA (US); Daniel Mark Spielman, Menlo Park, CA (US); Edith V. Sullivan, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 266 days.

(21) Appl. No.: 10/105,028

(22) Filed: Mar. 22, 2002

(65) Prior Publication Data

US 2002/0173713 A1 Nov. 21, 2002

Related U.S. Application Data

(60) Provisional application No. 60/278,563, filed on Mar. 23, 2001.

(51) Int. Cl.$^7$ ................................................. A61B 5/05
(52) U.S. Cl. ...................... 600/410; 600/407; 600/408; 600/425; 382/260; 382/285; 382/302; 382/307
(58) Field of Search ................................. 600/407, 408, 600/410, 425, 411, 427; 382/260, 285, 302, 307

(56) References Cited

U.S. PATENT DOCUMENTS

| | | | | |
|---|---|---|---|---|
| 5,560,360 A | * | 10/1996 | Filler et al. | 600/408 |
| 5,617,861 A | * | 4/1997 | Ross et al. | 600/410 |
| 5,709,208 A | * | 1/1998 | Posse et al. | 600/410 |
| 6,181,134 B1 | * | 1/2001 | Wald | 324/307 |
| 6,347,239 B1 | | 2/2002 | Arnold et al. | 600/410 |
| 6,430,430 B1 | * | 8/2002 | Gosche | 600/410 |

OTHER PUBLICATIONS

Pfefferbaum et al. (in a paper entitled "*In vivo spectroscopic quantification of the N–acetyl moiety, creatine, and choline from large volumes of brain gray and white matter: Effects of normal aging*" published in Magn. Res. in Med. 41:276–284, 1999.

Lim, et al. in a paper entitled "*Estimating NAA in Cortical Gray Matter with Applications for Measuring Changes due to Aging*" published in MRM 37:372–377 1997.

Pfefferbaum et al. also (in another paper entitled "*In vivo brain concentrations of N–acetyl compunds, creatine, and choline in Alzheimer's disease*" published in Arch. Gen. Psychiatry 56:185–192, 1999.

(List continued on next page.)

*Primary Examiner*—Angela D. Sykes
*Assistant Examiner*—William Jung
(74) *Attorney, Agent, or Firm*—Lumen Intellectual Property Services, Inc.

(57) ABSTRACT

A non-invasive longitudinal method that is sensitive and objective for quantifying progressive loss of neurons in normal aging brains and brains that suffer from a neurodegenerative disease is provided. The method also provides clinicians, patients and drug companies with a method for evaluating the efficacy of various treatments and interventions by assessing a change in brain integrity. The method determines and localizes a change in brain integrity in a compartment of a brain from at least structural images and metabolite brain images, which are acquired for at least two time instances. The time period between two time instances is dependent on the disease pathology and disease progression and could, for instance, be at least 3 months between time instances as well as at least 6 or 12 months between time instances.

29 Claims, 8 Drawing Sheets

OTHER PUBLICATIONS

Adalsteinsson et al. in a paper entitled "*Three–dimensional spectroscopic imaging with time–varying gradients*" and published in Magn. Res. Med. 33:461–466, 1995.

Spielman et al. in a paper entitled "*Lipid–suppressed single– and multisection proton spectroscopic imaging of the human brain*" and published in J. Magn. Res. Imaging 2:253–262, 1992.

Soher et al. in a paper entitled *Quantitative proton MR spectroscopic imaging of the human brain* and published in Magn. Res. Med. 35:356–363, 1996.

Webb et al. in a paper entitled "*Rapid, Fully, Automatic, Arbitrary–Volume in Vivo Shimming*" and published in Magn. Res. in Med. 20:113–122 1991.

Spielman et al., in a paper entitled "*Quantitiative assessment of improve homogeneity using higher–order shims for spectroscopic imaging of the brain*" and published in Magn. Res. in Med. 40:376–382, 1998.

Gudbjartsson et al. in a paper entitled "*The Rician distribution of noisy MRI data*" and published in Magn. Res. Med. 34:910–914, 1995.

Lim et al. in a paper entitled "*Segmentation of MRI images into cerobrospinal fluid spaces, white and gray matter*" and published in J. Comput. Assit. Tomogr. 13:588–593, 1989.

Kittler et al. in a paper entitled "*Minimum error thresholding*" and published in Pattern Recognition, 19:41–47, 1986.

Otsu et al. in a paper entitled "*A threshold selection method from gray–level histograms*" and published in IEEE Trans. Systems Man and Cybernetics 9:62–66, 1979.

Golub et al. in a paper entitled "*The differentiation of pseudo–inverses and nonlinear least squares problems whose variables separate*" and published in SIAM J. Num. Anal, 10:413–432, 1973.

* cited by examiner

MAGNETIC RESONANCE SPECTROSCOPIC IMAGING METHOD TO MONITOR PROGRESSION AND TREATMENT OF NEURODEGENERATIVE CONDITIONS

CROSS-REFERENCE TO RELATED APPLICATIONS

This application is cross-reference to and claims priority from U.S. Provisional Application No. 60/278,563 filed Mar. 23, 2001, which is hereby incorporated by reference.

STATEMENT REGARDING FEDERALLY SPONSORED RESEARCH OR DEVELOPMENT

This invention was supported in part by grant numbers AG-11427, CA-48269 and RR-09874 from the National Institute of Health (NIH). The U.S. Government has certain rights in the invention.

FIELD OF THE INVENTION

This invention relates generally to magnetic resonance imaging (MRI) and magnetic resonance spectroscopy imaging (MRSI). More particularly, the invention relates to a magnetic resonance spectroscopic imaging method to monitor progression and treatment of neurodegenerative conditions.

BACKGROUND

The ability of magnetic resonance spectroscopy (MRS) to visualize and quantify different amino acids and metabolites in the living human brain offers the opportunity for studying normal development, the aging process and the pathophysiology of neurological and psychiatric diseases. Proper interpretation of the results, however, requires information about the composition of the underlying brain tissue being studied. A number of cross-sectional investigations have focused on identifying deficits in metabolite signals in either a normal brain or in Alzheimer's disease. For instance, Pfefferbaum et al. (in a paper entitled "In vivo spectroscopic quantification of the N-acetyl moiety, creatine, and choline from large volumes of brain gray and white matter: Effects of normal aging" published in Magn. Res. in Med. 41:276–284, 1999) reports a cross-sectional study using volumetric proton resonance spectroscopic imaging (MRSI) to generate brain metabolite maps of normal brains in young and elderly subjects. Pfefferbaum et al. also (in another paper entitled "In vivo brain concentrations of N-acetyl compunds, creatine, and choline in Alzheimer's disease" published in Arch. Gen. Psychiatry 56:185–192, 1999) reported in a cross-sectional study that the gray matter N-acetyl compound concentrations, i.e. the signal intensity corrected for the amount of brain tissue contributing to the magnetic resonance spectroscopic imaging signal, was significantly reduced in patients with Alzheimer's disease.

U.S. Pat. No. 5,617,861 to Ross et al. disclosed a MRS analysis as a diagnostic tool for Alzheimer's disease. The method disclosed by Ross et al. provides a fairly rough cross sectional method to determine whether Alzheimer's disease might be present or not. This is accomplished by comparing the relative peak heights of myo-inositol relative to creatine and N-acetyl aspartate relative to creatine in the patient to the relative peak heights of myo-inositol relative to creatine and N-acetyl aspartate relative to creatine for a normal population, wherein an increase in the relative peak height of myo-inositol and a decrease in the relative peak height of N-acetyl aspartate is diagnostic of Alzheimer Disease.

U.S. Pat. No. 6,181,134 to Wald disclosed a method of obtaining the distribution of N-acetyl aspartate in mammalian neuronal tissue. The method includes the steps of: a) exciting the neuronal tissue to generate magnetic resonance signals, including signals corresponding to N-acetyl aspartate; b) suppressing non-N-acetyl aspartate magnetic resonance signals by a combination of band selective inversion with gradient de-phasing, and chemical shift selective pre-excitation; c) encoding a first spatial dimension of the N-acetyl aspartate signal with readout encoding and a second spatial dimension of the N-acetyl aspartate signal with gradient phase encoding, and d) using the encoded first and second spatial dimensions to image, by reconstruction, the distribution of N-acetyl aspartate in the tissue.

U.S. Pat. No. 6,347,239 to Arnold et al. disclosed a fairly rough method to measure in vivo the effect of a drug on the function of the nerve cells of the brain of a patient suffering from a neurological disease. In particular, Arnold's method focuses on N-acetyl aspartate and includes the steps of: a) measuring N-acetyl aspartate signal intensity using MRS of the brain of the patient; b) subjecting the patient to a treatment with the drug to be tested and measuring N-acetyl aspartate signal intensity using MRS of the brain of the patient; and c) comparing the spectra of steps a) and b) to determine whether the drug has an effect on the function of the nerve cells of the brain; whereby the increase in the NAA signal of step b) is indicative of a drug with a positive effect.

Unfortunately, although previous methods provide diagnostic tools to assess loss of neuronal tissue in normal aging brain or Alzheimer's disease patients, these methods do not provide a prospective method to adequately track changes of neuronal tissue over time in a sensitive and objective manner. Often in-vivo diagnostic MRS studies report N-acetyl aspartate as ratios of creatine or choline, even though both metabolites can change with age or disease, and thereby ignore the tissue composition of the regions measured, despite differences in N-acetyl aspartate concentration in gray matter and white matter. The development of a sensitive and objective method to non-invasively track changes of biochemical markers over time in normal aging and patients with a neurodegenerative disease is important for physicians and scientists that need to assess the progression of neuronal and functional deterioration or recovery, for instance to assess the efficacy of various types treatments, therapies or drugs that could potentially affect the neurodegenerative process. Accordingly, a prospective method that provides the best method to track changes in normal aging and patients with a neurodegenerative disease, has yet to be developed for volumetric MRSI to measure metabolite concentrations in different compartment of a mammalian brain.

SUMMARY OF THE INVENTION

The present invention provides a sensitive, objective and safe method for quantifying progressive loss of neurons over a disease course, and possible relay or reversal with treatment. The present invention also provides clinicians, patients and drug companies with a method for evaluating the efficacy of various treatments and interventions. More specifically, the present invention is a non-invasive method to determine and localize a change in brain integrity in a compartment of a brain. In the present invention, brain integrity is defined as the concentration of one or more neuronal markers, either separate or in combination, in a specific compartment of a mammalian brain. The method of the present invention is based on using at least structural images and metabolite brain images. These images are acquired for at least two time instances. The acquired structural and metabolic brain images for each time instance are then aligned. The aligned images for each time instance are then segmented in one or more compartments. Specific tissue compartments from which brain integrity is assessed are, for instance, gray matter, white matter or cerebrospinal fluid volume. However, the brain regions most susceptible to, for instance, Alzheimer's disease pathology are the hippocampus and surrounding gray matter, entorhinal cortex and temporal neocortex. As Alzheimer's disease progresses the parietal and frontal association cortices become involved. Therefore, anatomical targeting of the method of the present invention to these circumscribed regions of gray matter are also included. In general, the type of tissue and compartment that is selected to be localized and determined for a change in brain integrity is dependent on the disease pathology and disease progression. The method of the present invention further includes the step of determining the change in brain integrity over at least two times instances in one or more compartments of a brain. The time period between two time instances is dependent on the disease pathology and disease progression and could, for instance, be at least 3 months between time instances as well as at least 6 or 12 months between time instances. The present invention also includes a non-invasive method of assessing the efficacy of a treatment over a course of a treatment. The treatment is defined as at least two interventions at different time instances. The efficacy is determined and localized by a change in brain integrity in a compartment of a brain over the course of the treatment.

In view of that which is stated above, it is the objective of the present invention to provide a non-invasive method to determine and localize a change in brain integrity in a compartment of a brain from at least structural and metabolite brain images.

It is still another objective of the present invention to assess a change in brain integrity by determining N-acetyl aspartate.

It is still another objective of the present invention to assess a change in brain integrity by determining a combination of neuronal markers.

It is still another objective of the present invention to provide a method to asses a change in brain integrity over a period of at least 3, 6 or 12 months.

It is yet another objective of the present invention to assess a change in brain integrity of a normal aging brain.

It is yet another objective of the present invention to assess a change in brain integrity of a brain of a patient with a neurodegenerative disease.

It is yet another objective of the present invention to assess the efficacy of a treatment over a course of a treatment by determining and localizing a change in brain integrity.

The advantage of the present invention is that it provides a non-invasive longitudinal method that is sensitive and objective for quantifying progressive loss of neurons in normal aging brains and brains that suffer with a neurodegenerative disease. Another advantage of the present invention is that it provides clinicians, patients and drug companies with a method for evaluating the efficacy of various treatments and interventions by assessing a change in brain integrity.

BRIEF DESCRIPTION OF THE FIGURES

The objectives and advantages of the present invention will be understood by reading the following detailed description in conjunction with the drawings, in which.

DETAILED DESCRIPTION OF THE INVENTION

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

The present invention provides a non-invasive method to determine and localize a change in brain integrity in a compartment of a brain. In the present invention, brain integrity is defined as the concentration of one or more neuronal markers, either separate or in combination, in a specific compartment of a mammalian brain. Neuronal markers that are, for instance, but not limited to, N-acetyl aspartate, creatine, choline or myo-inositol. Specific tissue compartments from which brain integrity is assessed are, for instance, gray matter, white matter or cerebrospinal fluid volume. However, the brain regions most susceptible to, for instance, Alzheimer's disease pathology are the hippocampus and surrounding gray matter, entorhinal cortex and temporal neocortex. As Alzheimer's disease progresses the parietal and frontal association cortices become involved. Therefore, anatomical targeting of the method of the present invention to these circumscribed regions of gray matter are also included. In general, the type of tissue and compartment that is selected to be localized and determined for a change in brain integrity is dependent on the disease pathology and disease progression. The present invention is described for purposes of illustration only according to an exemplary embodiment related to Alzheimer's disease. Therefore, the present invention is not limited to determining and localizing a change in brain integrity in a compartment of a brain of an Alzheimer's disease patient, and could therefore also be used for a normal aging brain or a brain that suffers from a neurodegenerative condition such as, for instance, associated with AIDS, stroke, multiple sclerosis, amyotrophic lateral sclerosis or epilepsy.

Figure 1:
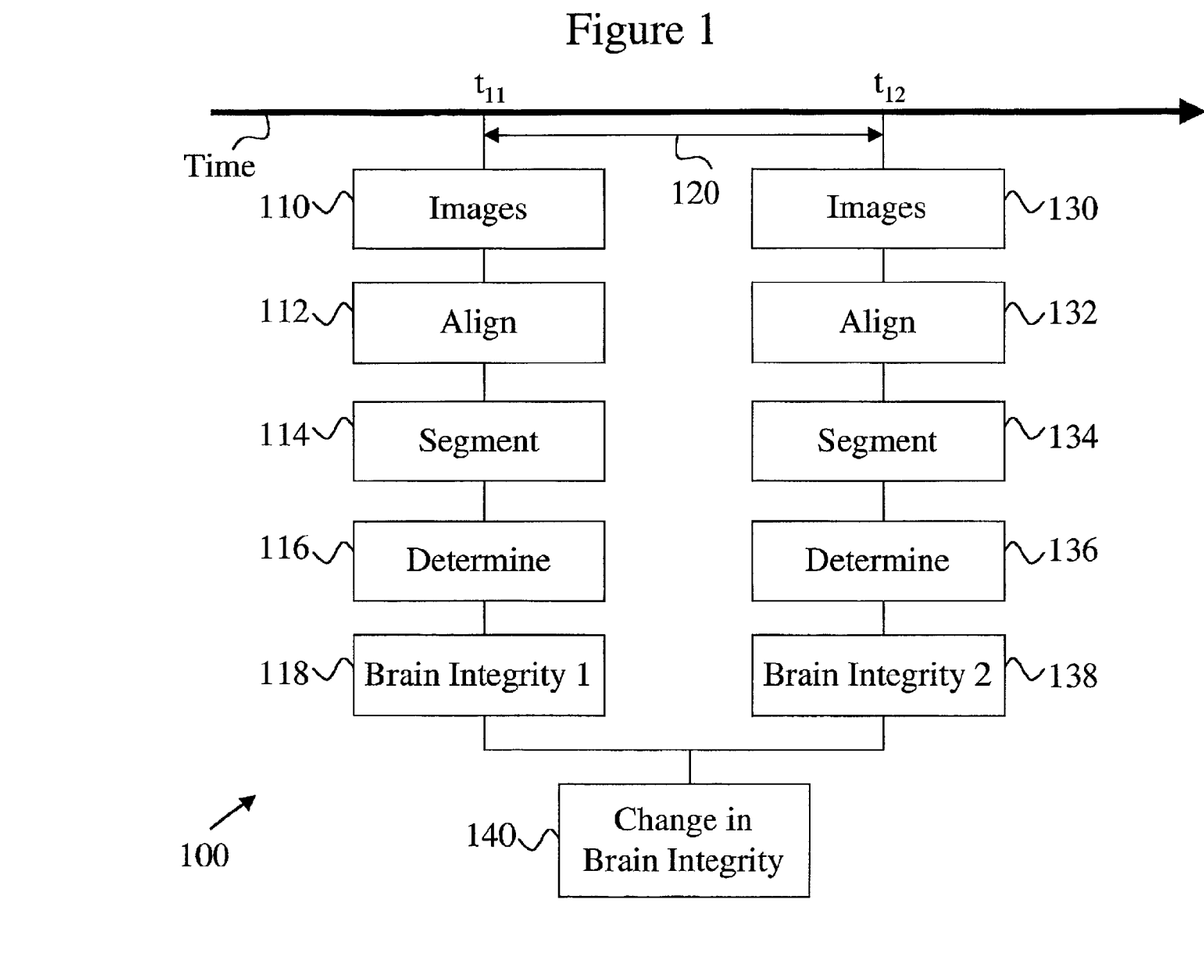
FIG. 1 shows a non-invasive method to determine and localize a change in brain integrity in a compartment of a brain according to the present invention.

FIG. 1 shows the non-invasive method 100 of the present invention to determine and localize a change in brain integrity 140 in a compartment of a brain. The change in brain integrity 140 is determined over a specific period of time covering at least two time instances. FIG. 1 shows two time instances, i.e. $t_{11}$ and $t_{12}$, over which change in brain integrity 140 is determined.

The change in brain integrity 140 is, for instance, the difference in brain integrity 1 118 and brain integrity 2 128, respectively determined at $t_{11}$ and $t_{12}$, or the rate of change in brain integrity over $t_{11}$ and $t_{12}$. As one skilled in the art might readily appreciate, several different measures could be obtained to assess a change in brain integrity 140 and are not limited to the difference or the rate of change. The time period 120 between $t_{11}$ and $t_{12}$ is dependent on the disease pathology and disease progression and could for instance be at least 3 months between time instances as well as at least 6 or 12 months between time instances. As described below in an exemplary embodiment for Alzheimer's disease, a period of 12 months was used to detect a 12% decline in N-acetyl aspartate gray matter concentration in Alzheimer's disease compared to a 0.3% decline in the same measure in normal controls.

Images 110, 130 are obtained at time instances $t_{11}$ and $t_{12}$, respectively, from a plurality of slices of the brain. Images 110, 130 include structural images and metabolite brain images. Spatial frequency matching of structural magnetic resonance (MR—dual echo fast spin echo) images and MR spectroscopic images (MRSI—obtained using oscillating readout gradients for efficient contiguous volumetric coverage of the brain) are performed to provide an estimate of the brain integrity 118, 138 within each spectroscopic voxel. Field map data could also be used as images 110, 130 to identify and include/exclude voxels that deviate from specified field uniformity criterion. Once the structural and metabolite brain images 110, 130 are acquired at respectively $t_{11}$ and $t_{12}$ they are aligned 112, 132 to create aligned images, i.e. images 110 (structural, metabolite and/or fieldmaps) are aligned, and images 130 (structural, metabolite and/or fieldmaps) are aligned. Using the aligned images, one or more compartments are segmented 114, 134 at respectively $t_{11}$ and $t_{12}$. Using the segment compartments, brain integrity 116, 136 is determined at respectively $t_{11}$ and $t_{12}$. Brain integrity 116, 136 is then used and compared to determine a change in brain integrity 140 over $t_{11}$ and $t_{12}$ for one or more compartments.

Figure 2:
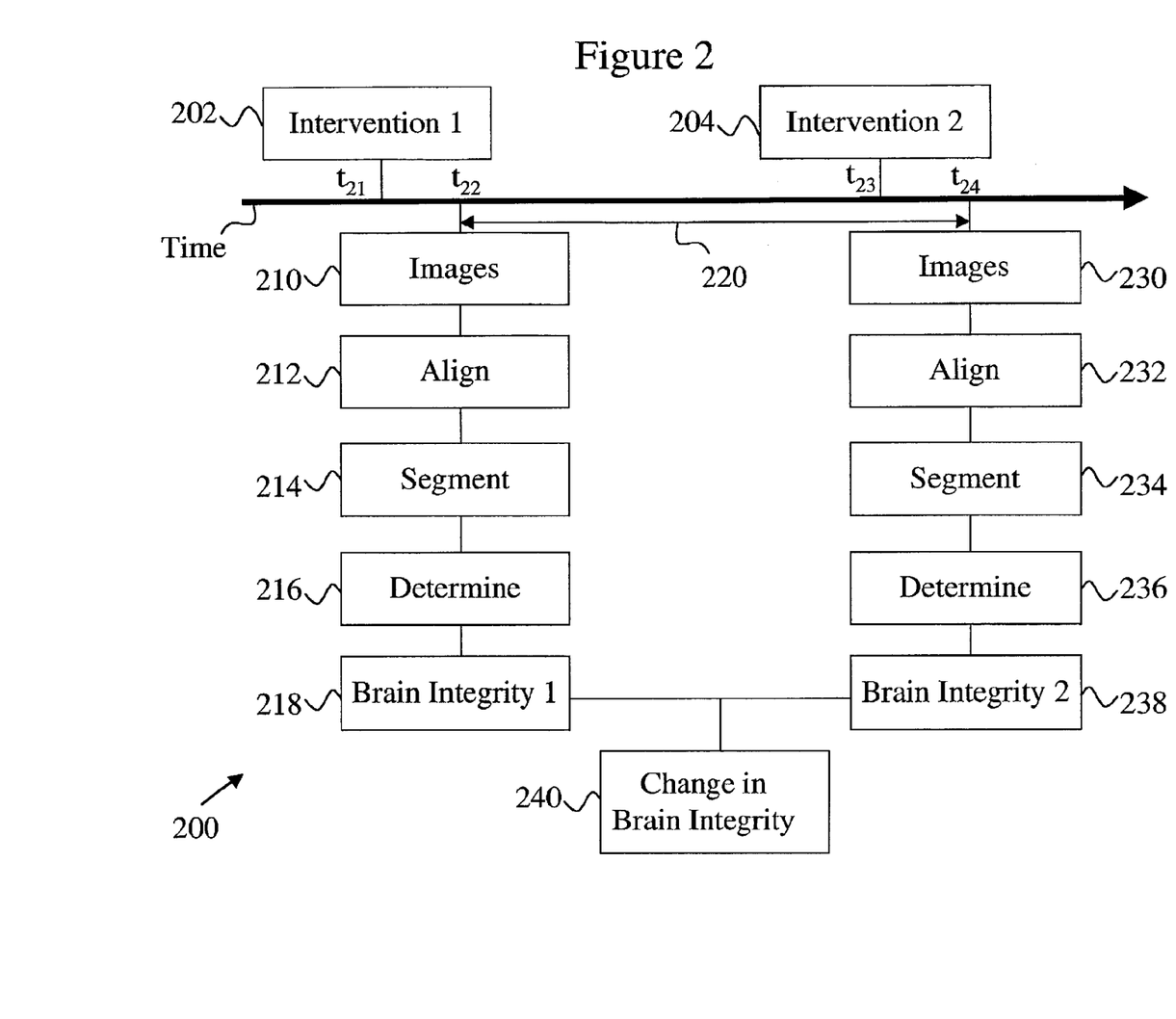
FIG. 2 shows a non-invasive method of assessing the efficacy of a treatment over a course of a treatment according to the present invention.

FIG. 2 shows a non-invasive method 200 of assessing the efficacy of a treatment over a course of a treatment. Treatment in the present invention is defined as at least two interventions that might affect the brain integrity. For instance, FIG. 2 shows two interventions at time instances $t_{21}$ and $t_{23}$. The time period 220 is dependent on the disease pathology and disease progression, as well as the type of treatment, and could for instance be at least 3 months between time instances as well as at least 6 or 12 months between time instances. The method of assessing the efficacy of a treatment is similar to the method 100 described in FIG. 1. The difference between FIG. 1 and FIG. 2 is that before the assessment of brain integrity at time instances $t_{22}$ and $t_{24}$ in FIG. 2, a treatment 202, 204 has taken place at respectively time instance $t_{21}$ and $t_{23}$. A treatment is, for instance, a drug therapy, medical intervention, psychotherapy or a psychiatric treatment. However, a treatment is not limited to these type of treatments as it could also be, for instance, a cell tissue implant. The acquisition of images 210, 230 takes place once intervention 202, 204 have taken effect, respectively. In the example of FIG. 2, images 210, 230 are obtained at time instances $t_{22}$ and $t_{24}$, respectively, from a plurality of slices of the brain as described above. Once the structural and metabolite brain images 210, 230 are acquired at respectively $t_{22}$ and $t_{24}$ they are aligned 212, 232 to create aligned images, i.e. images 210 (structural, metabolite and/or fieldmaps) are aligned, and images 230 (structural, metabolite and/or fieldmaps) are aligned. Using the aligned images, one or more compartments are segmented 214, 234 at respectively $t_{22}$ and $t_{24}$. Using the segment compartments, brain integrity 216, 236 is determined at respectively $t_{22}$ and $t_{24}$. Brain integrity 216, 236 is then used and compared to determine a change in brain integrity 240 over $t_{22}$ and $t_{24}$ for one or more compartments. Details about the possible image acquisition and analysis, as they are related to the description of FIGS. 1 and 2, are described below.

Image Acquisition.

$^1$H MR and MRS scans could, for instance, be acquired using a quadrature head coil on a 1.5 Tesla GE Signa MRI scanner with Echo-Speed gradient hardware (2.2 G/cm maximum gradient amplitude, and 185 ms minimum rise time). The data for the images could be obtained with oblique anatomic prescriptions parallel to the anterior-posterior commissure (AC-PC) line identified from midsagittal structural images.

Spectroscopic Image Acquisition.

A modified version of a 3D spectroscopic imaging sequence using a time-varying readout gradient in the slice selection direction could be used to image multiple contiguous slices (See e.g. Adalsteinsson et al. in a paper entitled "*Three-dimensional spectroscopic imaging with time-varying gradients*" and published in Magn. Res. Med. 33:461–466, 1995). Excitation could be accomplished with a pair of spin-echo spectral-spatial pulses whose spectral profile excites only the metabolites of interest while simultaneously suppressing the water resonance. The spatial profile of the pulses could then excite an approximately 5.5 cm thick slab in the longitudinal direction (z). An adiabatic inversion pulse presented 170 ms prior to the excitation pulse could be used to suppress lipid signals (See e.g. Spielman et al. in a paper entitled "*Lipid-suppressed single- and multisection proton spectroscopic imaging of the human brain*" and published in J. Magn. Res. Imaging 2:253–262, 1992). The $k_x$ and $k_y$ dimensions could be sampled by phase encoding prior to readout. A total of 256 phase encodes could be acquired with two averages. The $k_z$ and $k_f$ dimensions could be gridded, and the combined ($k_x, k_y, k_z, k_f$)-data could be Fourier transformed, as described in, for instance Adalsteinsson et al. (same paper as mentioned above). Exemplary collection parameters are, for instance, TR=2 s, TI=170 ms, TE=144 ms, FOV=24 cm. The nominal voxel size could be 1.1 cm$^3$, based on a 16 pixel sampling in $k_z$ over a 10.24 cm FOV, and an 18 pixel circular sampling in ($k_x, k_y$) over a 24 cm FOV.

Separate metabolite images, for instance for N-acetyl aspartate, creatine, choline and myo-inositol, could be produced by fitting a Gaussian lineshape to the magnitude spectrum from each voxel, where the line width of the Gaussian model could, for instance, be 8 Hz (measured as full width at half maximum). An estimate of the residual main field inhomogeneity could be formed for each voxel by using N-acetyl aspartate, creatine, choline and myo-inositol as internal reference signals to determine bulk shifts in the main field. Metabolite signal levels could then be displayed in, for instance, a 32×32 pixel image format for each slice and metabolite. The final metabolite images are then 16 slices of 32×32 pixels each.

Corrections for receiver gain and coil loading could be made when images are reconstructed (Soher et al. in a paper entitled "*Quantitative proton MR spectroscopic imaging of the human brain*" and published in Magn. Res. Med. 35:356–363, 1996) to allow comparability of metabolite signal levels between subjects. The correction for coil loading could be based on the radio frequency (RF) power required for a 90 degree flip angle as could be determined by the transmitter gain setting of the automatic pre-scan routine. A fixed transmitter gain value could be used as a reference, and studies with different gains could be scaled proportional to the difference in RF power required to obtain a 90 degree flip angle. Thus, as in (Soher et al. 1996, same reference as mentioned above):

$$S_{corr} = S_{uncorr} \cdot 10^{\frac{A}{20}}$$

where $S_{corr}$ and $S_{uncorr}$ are the corrected and uncorrected signal values, and A is the difference in RF power (in dB) between the reference transmitter gain and the value required for the data being corrected. This approach to coil loading was validated in Soher et al. (1996, same reference as mentioned above), where phantom experiments were performed over a wide range of transmitter gain values on the same type of hardware as could be used for the present invention. It is the experience of the present inventors that there is little variation in transmitter power from one subject to another, and the resulting correction factor is typically in the range from 0.9 to 1.1.

Shimming and Fieldmap Acquisition.

Automated shimming, for instance, based on 32 slices (each 0.64 cm thick) 25.6 mm above the AC-PC line, could include a B0 fieldmap (measured from the high signal-to-noise ratio water image) and a least-squares fitting procedure (See, for instance, Webb et al. in a paper entitled "*Rapid, Fully, Automatic, Arbitrary-Volume in Vivo Shimming*" and published in Magn. Res. in Med. 20:113–122 1991). Gradient coils provide the linear terms and a computer-controlled resistive shim supply provide higher order terms (xy, $x^2-y^2$, zx, zy, $z^2$, and $z^3$) which typically increase the number of usable spectroscopic voxels by 30% over the linear terms (Spielman et al., in a paper entitled "*Quantitative assessment of improved homogeneity using higher-order shims for spectroscopic imaging of the brain*" and published in Magn. Res. in Med. 40:376–382, 1998). After the desired shim is achieved, a final 3D fieldmap could be collected at a resolution of 64×64×32 (TR=40, TE=10, flip angle=20∞, effective slice thickness 6.4 mm, FOV=24 cm, matrix 64×64) in order to measure residual field inhomogeneities.

Structural Image Acquisition.

The midsagittal slice of a sagittal gradient recalled echo scout series (TR=50 ms, TE 6 ms, flip angle=30∞, 5 mm skip 2.5 mm, NEX=1, time=30 s) could be used to compute slice positions with 0.5 mm accuracy for all three scans in the method of the present invention, i.e. anatomical, fieldmap and MRSI scans. Anatomic images could be acquired with an axial fast spin echo (FSE) protocol (for instance with TR=3000 ms, TE=20/80 ms, echo train length=8, 3 mm slices skip 0.2 mm; 256×256 matrix, 24 cm FOV, NEX=1, time=3:18 min). For instance, but not limited to, sixteen slices could be collected, the most inferior slice beginning at the AC-PC line, corresponding to the 8 middle spectroscopic slices and providing two anatomic slices for each MRS slice.

Spectroscopic Images Analysis.

For instance, but not limited to, six slices of MRS data could be used beginning with the slice 12.8 mm above the anterior-posterior (AC-PC) line and extending superiorly. These slices could be chosen because they had the least amount of signal loss and artifacts due to field inhomogeneity. Within these six slices, only pixels with good homogeneity (B0 shifts within a ±5 Hz range) should be included for analysis. These slices could also be manually edited to remove regions, usually outside of the brain, of obvious lipid and/or water artifact. To further guard against the possibility that incompletely suppressed water signal contaminated the MRS data, especially for choline and creatine in the medial frontal region, an exclusion region of interest roughly corresponding to the cingulate gyrus could be constructed for each slice by proportional geometric positioning.

The metabolite signals could be calculated as magnitude values, so the noise in the metabolite maps has a non-Gaussian (Rician) noise distribution in the low-SNR range. To account for the effects of this non-Gaussian noise distribution, a bias correction could be applied to the metabolite signal intensity values, by for instance:

$$\text{metabolite}_{corrected} = \sqrt{\text{metabolite}^2 - \sigma^2} \quad (1)$$

where $\sigma^2$ is an estimate of the noise variance from a sample of non-brain pixels (See Gudbjartsson et al. in a paper entitled "*The Rician distribution of noisy MRI data*" and published in Magn. Res. Med. 34:910–914, 1995).

Structural Images Analysis.

Using the dual echo FSE data, the non-brain (i.e., dura, skull and scalp) tissue could be stripped away leaving each slice composed of gray matter, white matter, (Lim et al. in a paper entitled "*Segmentation of MRI images into cerobrospinal fluid spaces, white and gray matter*" and published in J. Comput. Assist. Tomogr. 13:588–593, 1989) or cerebrospinal fluid (CSF). Segmentation could follow the procedure of Lim et al. (1989, same reference as above) wherein low frequency variation across the image could be removed with homomorphic high pass filtering followed by minimum error thresholding to separate tissue from CSF on early-minus-late echo difference images (Kittler et al. in a paper entitled "*Minimum error thresholding*" and published in Pattern Recognition, 19:41–47, 1986) and then non-parametric histogram separation of gray matter and white matter from early-plus-late echo summation images (Otsu et al. in a paper entitled "*A threshold selection method from gray-level histograms*" and published in IEEE Trans. Systems Man and Cybernetics 9:62–66, 1979). Misclassification, especially of white matter hyper-intensities, could be manually corrected. The images could then be converted into segmentation maps with each voxel designated as either gray matter, white matter, or CSF (the contribution from blood vessels could be ignored). The data from each of the two segmented high resolution structural slices corresponding to a metabolite slice could then be combined to provide 128 (8×8×2) segmented voxels underlying each metabolite voxel. The total number of high resolution voxels of each type (gray matter, white matter, and CSF) across the analyzed slices, independent of metabolite exclusion criteria, is then computed to provide an estimate of the brain tissue composition. A similar measure for only the voxels included in the metabolite analysis is also computed.

Spatial Frequency Filtering.

The segmented structural images are used to create a separate gray matter image and white matter image. The spatial frequency characteristics of the two different tissue maps (i.e. gray matter and white matter) could be made to match those of the MRS data on an axial slice by slice basis; the z-axis (i.e., across slices) characteristics could be ignored. The tissue map could be Fourier transformed to the frequency domain, the inner 32×32 matrix identified, a filter template matching the frequency characteristics of the MRS data could be applied. The results would then, in this example, return as a 32×32 complex array.

Structural/Metabolite Image Analysis.

The model, based on magnitude spectra, for the determination of the contribution of gray and white matter tissue to the signal observed for metabolite M (where M is N-acetyl asparate, creatine, choline and myo-inositol) in the ith voxel is:

$$y_i = |g_i \cdot M_g + w_i \cdot M_w| + n_i \quad (2)$$

where $y_i$ is the measured data for the metabolite, $M_w$ and $M_g$ are the white matter and gray matter contributions of the metabolite signal M, $g_i$ and $w_i$ are the low-pass filtered structural representation of the gray matter and white matter tissues, and $n_i$ is additive noise.

In general, finding the optimal values of $M_g$ and $M_w$ involves a nonlinear two-dimensional search. However, assuming that $M_w > 0$ yields:

$$y_i = M_w |g_i \cdot r_{gw} + w_i| + n_i \quad (3)$$

where $r_{gw}$ is the gray to white matter metabolite ratio, $M_g/M_w$. With this formulation, one need only estimate one linear parameter, $M_w$, and one nonlinear parameter, $r_{gw}$. Using the method of variable projection by Golub (Golub et al. in a paper entitled "*The differentiation of pseudo-inverses and nonlinear least squares problems whose variables seperate*" and published in SIAM J. Num. Anal, 10:413–432, 1973), the least squares solution could be found by first expressing the estimate $\tilde{M}_w$ assuming $r_{gw}$ is known, i.e.

$$\tilde{M}_w = \frac{\sum_{i=1}^{N} f_i \cdot y_i}{\sum_{i=1}^{N} f_i^2} \quad (4)$$

where $$f_i = |g_i \cdot r_{gw} + w_i| \quad (5)$$

and N is the total number of spectroscopic voxels. The estimated gray to white matter ratio, $\tilde{r}_{gw}$, could then be found by substituting Equation 4 into Equation 3 and minimizing:

$$\min_{r_{gw}} \sum_{i=1}^{N} (y_i - \tilde{M}_w f_i)^2 \quad (6)$$

The least squares solution, given by Equations 4 and 6, is optimal for additive Gaussian noise. However, for this low SNR data the noise is actually Rician distributed and, while a bias correction was made as described by Equation 1, one would experience that minimizing the absolute error:

$$\min_{r_{gw}} \sum_{i=1}^{N} |y_i - \tilde{M}_w f_i| \quad (7)$$

rather than the square error to be more robust to outliers in the data. Once the optimum value of $\tilde{r}_{gw}$ is determined for each subject, white matter metabolite intensity values could be determined using Equation 4 and gray matter values could be found by the expression:

$$\tilde{M}_g = \tilde{M}_w \cdot \tilde{r}_{gw} \quad (8)$$

Figure 3A:
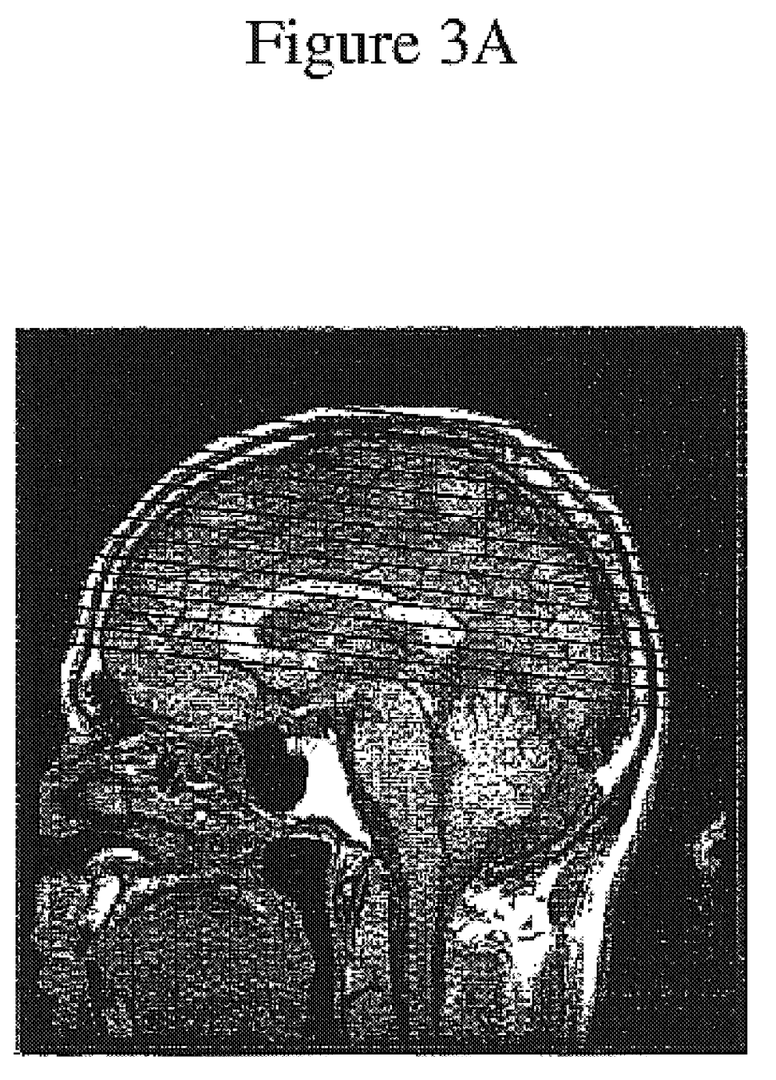
FIG. 3A shows an example of in-vivo images acquired with echo-planar spectroscopic imaging according to the present invention.
Figure 3B:
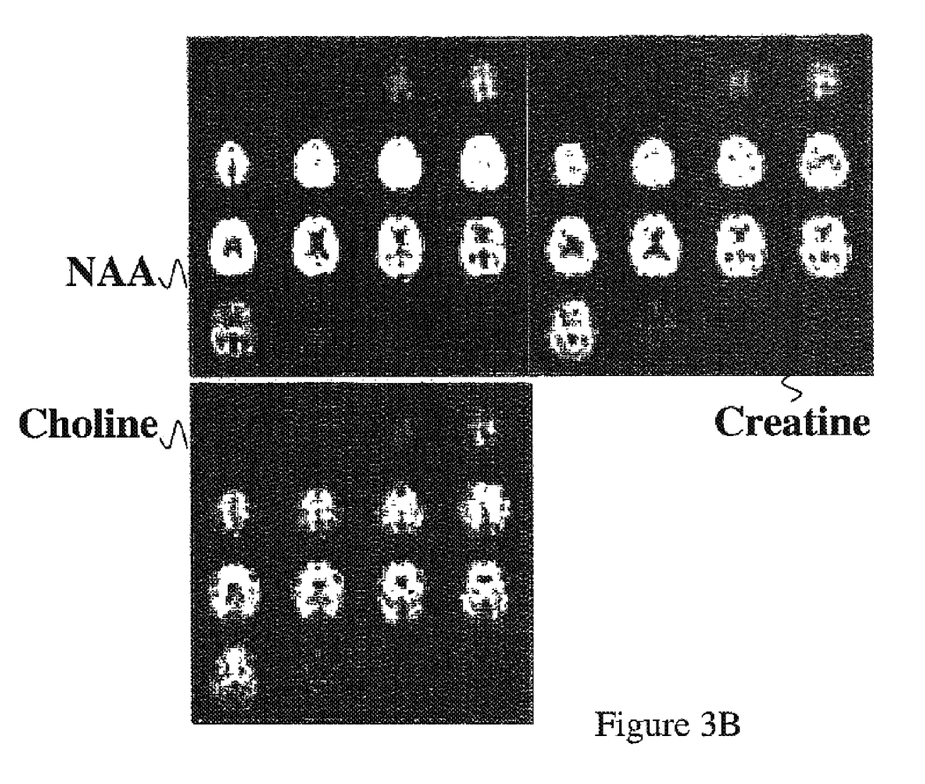
FIG. 3B shows reconstructed N-acetyl asparate (NAA), creatine (Cr) and choline (Ch) images using the images acquired in FIG. 3A.
Figure 4:
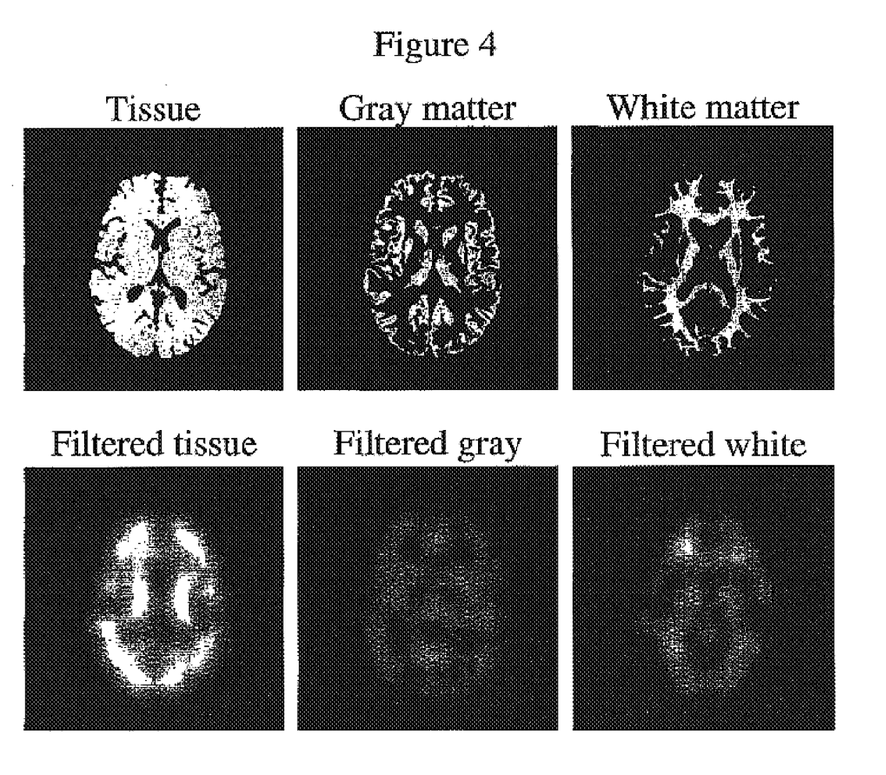
FIG. 4 shows an example of a segmented image and spatial filtering to match the spatial frequency content of the high-resolution structural data with the low-resolution metabolite images according to the present invention.
Figure 5:
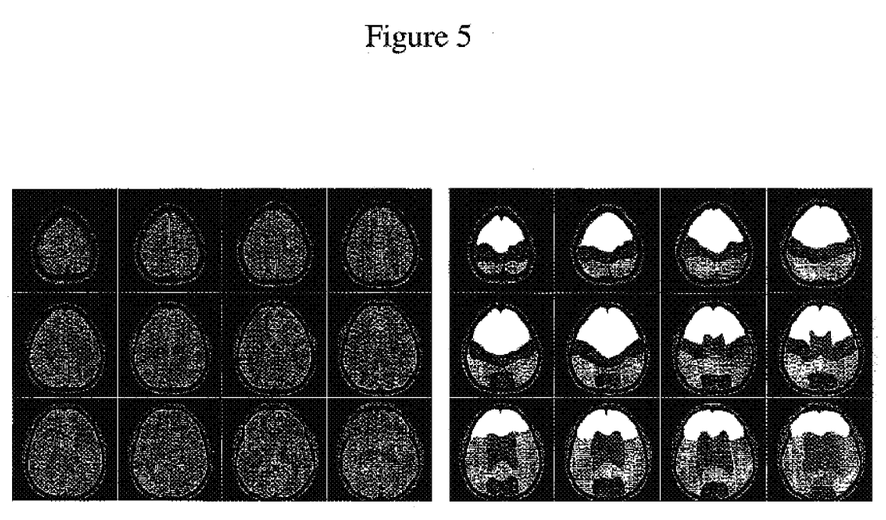
FIG. 5 shows an example of regions for further compartmental analysis of metabolite concentrations based on combining structural and metabolite information according to the present invention.

FIG. 3A shows an example of in-vivo images acquired with echo-planar spectroscopic imaging. Image data was acquired at an oblique-axial orientation. From these acquired images, N-acetyl asparate (NAA), creatine (Cr) and choline (Ch) was reconstructed as shown in FIG. 3B. FIG. 4 shows an example of a segmented image and spatial filtering to match the spatial frequency content of the high-resolution structural data with the low-resolution metabolite images. FIG. 5 shows an example of regions for further compartmental analysis of metabolite concentrations based on combining structural and metabolite information.

Figure 6:
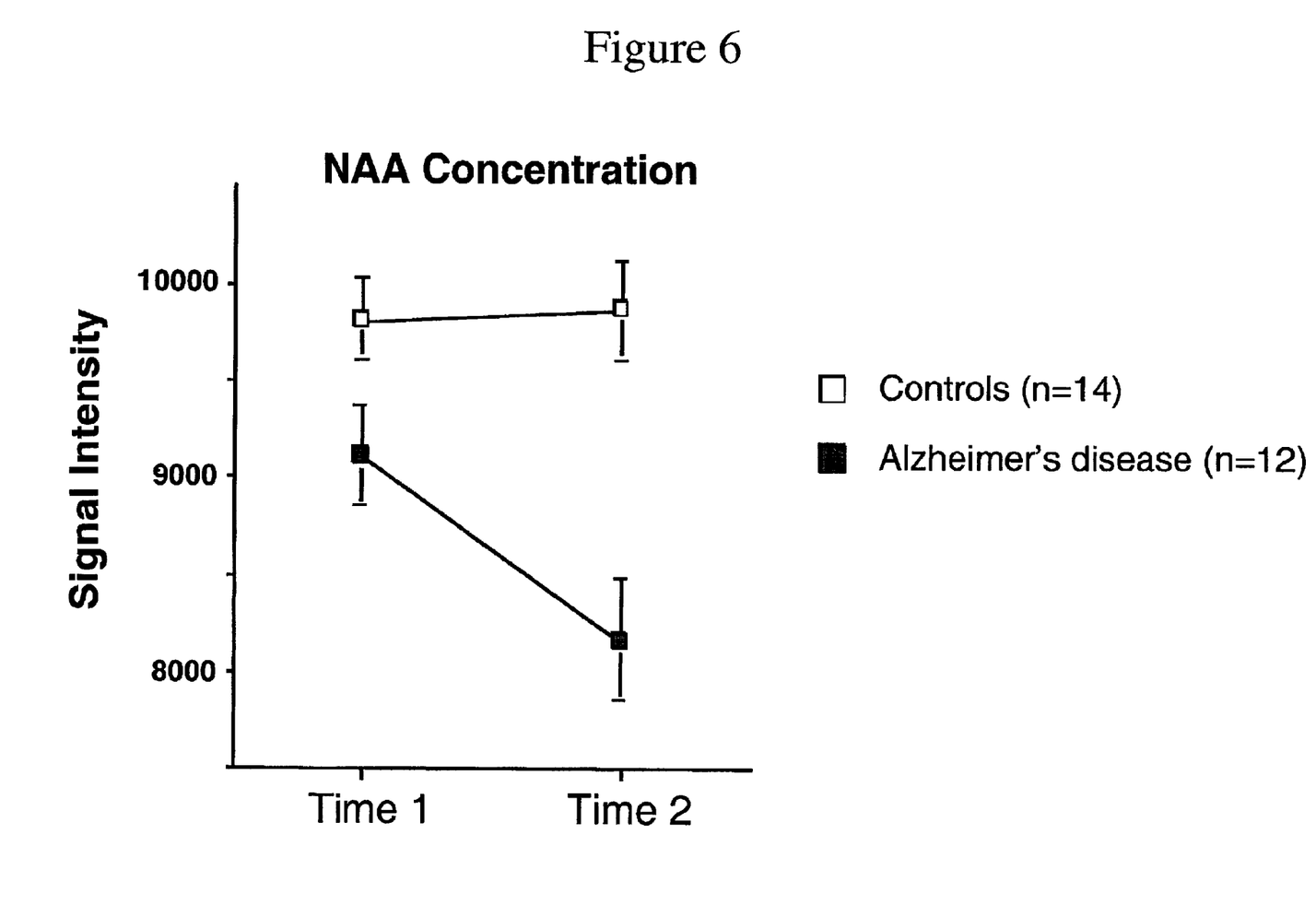
FIG. 6 is an exemplary embodiment of the method of the present invention showing the result of a 12% decline in N-acetyl aspartate gray matter concentration in Alzheimer's disease over a 12 month period according to the present invention.

FIG. 6 is an exemplary embodiment of the method of the present invention showing the result of a 12% decline in N-acetyl aspartate gray matter concentration in Alzheimer's disease over a 12 month period (difference between Time 1 and Time 2) compared to a 0.3% decline in the same measure in normal controls. The results in FIG. 6 were obtained from Alzheimer's disease patients (7 men, 5 women, 74±7 years; NINCDS-ADRDA criteria) and healthy elderly volunteers (7 men, 7 women, 73±4 years). For this particular example, the imaging protocol (1.5T GE Signa, standard head coil) included in-vivo shimming, fast spin-echo MRI (FSE, TE1/TE2/TR=20/80/3000 ms), volumetric MRSI with phase-encoding in-plane, and a time-varying readout gradient to encode the third spatial dimension (TE/TR=144/2000 ms; 1.1 cc voxel size; 17 min acquisition time). N-acetyl asparate images were estimated from magnitude spectra from 7 slices. Structural FSE data, fieldmaps, and metabolite images were aligned, and FSE images were segmented into gray matter, white matter, and cerebrospinal fluid. NAA concentrations were estimated separately in gray matter and white matter based on the assumption that $M_i = |g_i NAA_g + w_i NAA_w + n|$, where $M_i$ is the measured N-acetyl aspartate (NAA) magnitude for voxel i; $NAA_g$, $NAA_w$ are the desired gray and white matter signals per unit of tissue volume; $g_i$, $w_i$ are the gray and white matter fractions in the voxel i; and n is Gaussian noise. This model was fitted to the data with a maximum-likelihood solution, which takes into account the Rician-distributed noise in the low-SNR magnitude N-acetyl aspartate images.

To reduce the effects of B0 inhomogeneity on the signal estimates, only those voxels were included in the model that satisfied a field deviation of less than ±5 Hz (±0.08 ppm at 1.5T) as measured by the fieldmap. Data were adjusted for drift in absolute scanner signal intensity with a correction factor based on the regression of MRSI background noise on calendar time ($r^2 = 0.912$, third order polynomial) for 104 subjects scanned during the project period.

Repeated measures analysis of variance (ANOVA) revealed a significant group effect ($p<0.002$) and interaction ($p<0.025$), where the gray matter N-acetyl asparate in Alzheimer's disease patients was lower than that of the controls at both times and declined significantly over time in Alzheimer's disease patients but not in controls. This group difference in gray matter N-acetyl asparate concentration was also reflected in a comparison of percent change/year (mean±SD: Alzheimer's disease patients=−12.36±14.86; control=0.94±8.17), which accounted for individual differences in interscan interval (see FIG. 7). ANOVA effects were not significant for white matter N-acetyl asparate. In contrast to N-acetyl asparate, structural gray matter volumes (GM Volume) showed only nonsignificant declines (p<0.06, one-tailed) in the Alzheimer's disease patients relative to the control group, although the Alzheimer's disease group had significantly smaller gray matter volumes than the control group at both scan times (p<0.01 for each time).

DRS performance by the Alzheimer's disease group (−12±15 points) declined significantly more (p=0.01) than that of the control group (−0.3±2 points), and percent change per year in DRS scores correlated modestly with N-acetyl aspartate gray matter concentration decline (r=0.54, p<0.05, one-tailed).

The two other prominent metabolites at late echo times are creatine and choline. In the Alzheimer's disease group, the gray-matter choline signal did not change over time (−0.3%, n.s.), whereas the gray-matter creatine like N-acetyl aspartate, showed a significant decrease (−9.3%, p=0.03). While there is considerable evidence that N-acetyl aspartate is a marker of neuronal viability, creatine changes are more difficult to interpret because the measured signal is the sum of creatine and phosphocreatine (low and high energy states), and creatine is a major metabolite in astrocytes and oliogondendrocytes as well as neurons.

Figure 7:
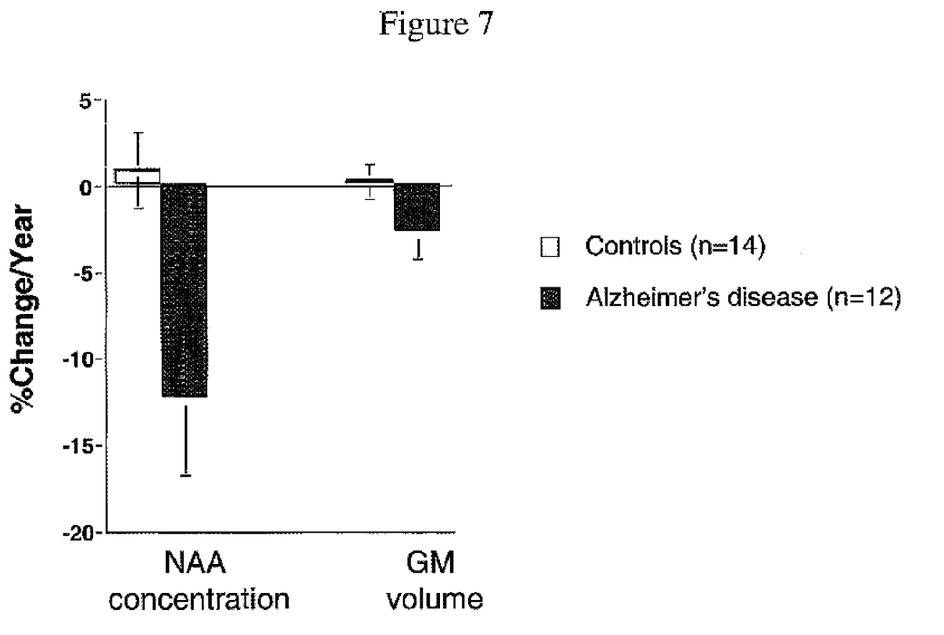
FIG. 7 shows an example of N-acetyl aspartate gray matter concentration and gray matter volume expressed as percent change per year according to the present invention.

FIGS. 6 and 7 show that a decline in NAA gray matter concentration is sensitive to neuronal and functional deterioration in mild to moderate Alzheimer's disease over a one-year interval. Further, reduction in N-acetyl aspartate gray matter concentration measured with MRSI is more sensitive to detection of decline than was structural gray matter volume measured concurrently with MRI. Thus, N-acetyl aspartate gray matter concentration is a suitable metric for the detection and monitoring of deterioration of neuronal integrity with Alzheimer's disease progression and possibly of improvement in neuronal function with treatment.

Furthermore, other proton metabolic markers, visible with alternative spectroscopic methods may provide additional information to the N-acetyl aspartate gray matter index that could increase the sensitivity of the present method. For example, myo-inositol is a marker of glial proliferation, which complements neuronal degeneration. It is present in glial but not glial neuronal cell cultures, has been described as a glial marker and is present in higher concentrations in gray matter than white matter. The measurement of a commensurate rise in myo-inositol and N-acetyl aspartate may be an especially powerful marker of neurodegeneration for tracking changes in Alzheimer's disease.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. All such variations are considered to be within the scope and spirit of the present invention as defined by the following claims and their legal equivalents.

What is claimed is:

1. A non-invasive method to determine and localize a change in brain integrity in a compartment of a brain wherein said brain integrity is the concentration of a neuronal marker in one or more structural compartments with a brain tissue type comprising the steps of:

(a) providing structural images said brain and metabolite images using MRS of said brain for at least two time instances, wherein said structural images provide information regarding brain tissue type and said one or more structural compartments and said metabolite brain images provide information regarding said concentration of said neuronal marker;

(b) aligning said structural brain images and said metabolic brain images and thereby creating aligned images;

(c) segmenting said one or more structural compartments with said specific brain tissue type from said aligned images and guided by said structural images, wherein said brain tissue type is selected from the group consisting of gray matter, white matter and cerebrospinal fluid;

(d) determining said change in brain integrity over said at least two times instances in said one or more structural compartments of said brain by determining the change in concentration of said neuronal marker per unit volume of said brain tissue type.

2. The method as set forth in claim 1, wherein said change in brain integrity is assessed by determining N-acetyl aspartate as a neuronal marker.

3. The method as set forth in claim 1, wherein said change in brain integrity is assessed by determining a combination of neuronal markers, wherein said neuronal markers are selected from the group consisting of N-acetyl aspartate, creatine, choline and myo-inositol.

4. The method as set forth in claim 1, wherein said at least two time instances are at least 3 months apart.

5. The method as set forth in claim 1, wherein said at least two time instances are at least 6 months apart.

6. The method as set forth in claim 1, wherein said at least two time instances are at least 12 months apart.

7. The method as set forth in claim 1, wherein said change in brain integrity is assessed from a normal aging brain.

8. The method as set forth in claim 1, wherein said change in brain integrity is assessed from a brain of a patient with a neurodegenerative condition wherein said neurodegenerative condition is selected from the group consisting of Alzheimer's disease, AIDS, stroke, multiple sclerosis, amyotrophic lateral sclerosis and epilepsy.

9. The method as set forth in claim 8, wherein the time between said at least two time instances is determined by the progression of said neurodegenerative condition.

10. The method as set forth in claim 1, wherein said step of determining said change in brain integrity comprises the step of fitting a model to said one or more compartments with a maximum-likelihood solution which takes into account a Rician-distributed noise on a low-signal-to-noise magnitude.

11. A non-invasive method to determine and localize a change in N-acetyl aspartate in a structural compartment of a brain characterized by a brain tissue type, comprising, the steps of:

(a) providing structural images using MRI of said brain and metabolite images using MRS of said brain for at least two time instances, wherein said structural images provide information regarding said brain tissue type and said structural compartments and said metabolite brain images provide information regarding said concentration of said N-acetyl as aspartate;

(b) aligning said structural brain images and said metabolic brain images and thereby creating aligned images;

(c) segmenting said structural compartment with said specific brain tissue type from said aligned images and guided by said structural images wherein said brain tissue type is selected from the group consisting of gray matter, white matter and cerebrospinal fluid; and (d) determining said change in N-acetyl aspartate over said at least two times instances in said structural compartment of said brain by determining said change in concentration of said N-acetyl asparate unit volume of said brain tissue type.

12. The method as set forth in claim 11, wherein said change in N-acetyl aspartate is assessed by determining said change in N-acetyl aspartate in combination with other neuronal markers, wherein said other neuronal markers are selected from the group consisting of creatine, choline and myo-inositol.

13. The method as set forth in claim 11, wherein said at least two time instances are at least 3 months apart.

14. The method as set forth in claim 11, wherein said at least two time instances are at least 6 months apart.

15. The method as set forth in claim 11, wherein said at least two time instances are at least 12 months apart.

16. The method as set forth in claim 11, wherein said change in N-acetyl aspartate is assessed from a normal aging brain.

17. The method as set forth in claim 11, wherein said change in N-acetyl aspartate is assessed from a patient with a neurodegenerative condition wherein said neurodegenerative condition is selected from the group consisting of Alzheimer's disease, AIDS, stroke, multiple sclerosis, amyotrophic lateral sclerosis and epilepsy.

18. The method as set forth in claim 17, wherein the time between said at least two time instances is determined by the progression of said neurodegenerative condition.

19. The method as set forth in claim 11, wherein said step of determining said change in N-acetyl aspartate comprises the step of fitting a model to said compartments with a maximum-likelihood solution which takes into account a Rician-distributed noise on a low-signal-to-noise magnitude.

20. A non-invasive method of assessing the efficacy of a treatment over a course of said treatment, wherein said treatment comprises at least two interventions at different time instances, by determining and localizing a change in brain integrity in a compartment of a brain wherein said brain integrity is the concentration of a neuronal marker in one or more structural compartments with a brain tissue type, comprising the steps of:

(a) providing structural images using MRI of said brain and metabolite images using MRS of said brain after each of said at least two interventions have taken effect, wherein said structural images provide information regarding brain tissue type and said one or more structural compartments and said metabolite brain images provide information regarding said concentration of said neuronal marker;

(b) aligning said structural brain images and said metabolic brain images and thereby creating aligned images;

(c) segmenting said one or more structural compartments with said specific brain tissue type from said aligned images and guided by said structural images, wherein said brain tissue type is selected from the group consisting of gray matter, white matter and cerebrospinal fluid; and (d) determining said change in brain integrity over said course of said treatment in said one or more structural compartments of said brain by determining said change in concentration of said neuronal marker per unit volume of said brain tissue type.

21. The method as set forth in claim 20, wherein said change in brain integrity is assessed by determining N-acetyl aspartate as neuronal marker.

22. The method as set forth in claim 20, wherein said change in brain integrity is assessed by determining a combination of neuronal markers, wherein said neuronal markers are selected from the group consisting of N-acetyl aspartate, creatine, choline and myo-inositol.

23. The method as set forth in claim 20, wherein said at least two interventions are at least 3 months apart.

24. The method as set forth in claim 20, wherein said at least two interventions are at least 6 months apart.

25. The method as set forth in claim 20, wherein said at least two interventions are at least 12 months apart.

26. The method as set forth in claim 20, wherein said change in brain integrity is assessed from a normal aging brain.

27. The method as set forth in claim 20, wherein said change in brain integrity is assessed from a brain of a patient with a neurodegenerative condition wherein said neurodegenerative condition is selected from the group consisting of Alzheimer's disease, AIDS, stroke, multiple sclerosis, amyotrophic lateral sclerosis and epilepsy.

28. The method as set forth in claim 27, wherein the time between said at least two time instances is determined by the progression of said neurodegenerative condition.

29. The method as set forth in claim 20, wherein said step of determining said change in brain integrity comprises the step of fitting a model to said one or more compartments with a maximum-likelihood solution which takes into account a Rician-distributed noise on a low-signal-to-noise magnitude.

* * * * *